(12) United States Patent
Cho et al.

(10) Patent No.: US 8,530,684 B2
(45) Date of Patent: Sep. 10, 2013

(54) METHOD FOR PREPARING FATTY ACID ALKYL ESTER USING FATTY ACID

(75) Inventors: Hyun-Jun Cho, Seoul (KR);
Byung-Hui Kim, Suwon-si (KR);
Soo-Hyun Kim, Incheon (KR);
Yong-Jun Shin, Seoul (KR); Shin-ho Chun, Seongnam-si (KR)

(73) Assignee: SK Chemicals Co., Ltd., Suwon-Si (KR)

( * ) Notice: Subject to any disclaimer, the term of this patent is extended or adjusted under 35 U.S.C. 154(b) by 187 days.

(21) Appl. No.: 12/934,923

(22) PCT Filed: Apr. 1, 2008

(86) PCT No.: PCT/KR2008/001831
§ 371 (c)(1),
(2), (4) Date: Sep. 27, 2010

(87) PCT Pub. No.: WO2009/123369
PCT Pub. Date: Oct. 8, 2009

(65) Prior Publication Data
US 2011/0028747 A1 Feb. 3, 2011

(51) Int. Cl.
*C11B 3/00* (2006.01)
(52) U.S. Cl.
USPC ............................................. 554/174
(58) Field of Classification Search
None
See application file for complete search history.

(56) References Cited

U.S. PATENT DOCUMENTS

| 4,164,506 A | 8/1979 | Kawahara et al. | |
|---|---|---|---|
| 4,594,441 A * | 6/1986 | Findeisen et al. | 560/25 |
| 4,608,202 A | 8/1986 | Lepper et al. | |
| 4,652,406 A | 3/1987 | Lepper et al. | |
| 5,849,939 A | 12/1998 | Mittelbach et al. | |
| 8,222,439 B2 * | 7/2012 | Glasl et al. | 554/169 |
| 2005/0027137 A1 | 2/2005 | Hooker | |
| 2005/0113588 A1 | 5/2005 | Hillion et al. | |
| 2006/0155138 A1 | 7/2006 | Haas et al. | |
| 2007/0260077 A1 | 11/2007 | Elliott | |
| 2008/0051592 A1 * | 2/2008 | McNeff et al. | 554/170 |

FOREIGN PATENT DOCUMENTS

| EP | 0 127 104 A | 12/1984 |
|---|---|---|
| EP | 0 184 740 B1 | 6/1986 |
| EP | 0 708 813 B1 | 5/1996 |

(Continued)

OTHER PUBLICATIONS

Hou, X. et al., Lewis acid-catalyzed transesterification and esterificatin of high free fatty acid oil in subcritical methanol, 2007, Korean J. Chem. Eng., 24(2), pp. 311-313.*

*Primary Examiner* — Yate K Cutliff
(74) *Attorney, Agent, or Firm* — Birch, Stewart, Kolasch & Birch, LLP

(57) ABSTRACT

A method for preparing fatty acid alkyl ester for bio-diesels is disclosed, wherein fatty acid, specifically fatty acid distillate reacts with alcohol in the presence of metal catalyst instead of conventional acid or solid acid catalyst. The method does not require the glycerin purification process, and has the superior conversion ratio of fatty acid. The method for preparing fatty acid alkyl ester comprises the step of carrying out an esterification reaction of fatty acid raw material with alcohol in the presence of metal catalyst. Preferably, the esterification reaction is carried out at the temperature of 200 to 350° C. and the pressure of atmospheric pressure to 10 bar, and the metal catalyst is a compound containing metal selected from the group consisting of cobalt, iron, manganese, zinc, titanium and mixture thereof.

2 Claims, 2 Drawing Sheets

(56) References Cited

FOREIGN PATENT DOCUMENTS

| JP | 2002-193882 A | 7/2002 |
| KR | 10-2004-0087625 A | 10/2004 |
| KR | 10-2007-0106236 A | 11/2007 |
| WO | WO 2005068593 A1 | 7/2005 |
| WO | 2007/126166 A1 | 11/2007 |

* cited by examiner

METHOD FOR PREPARING FATTY ACID ALKYL ESTER USING FATTY ACID

TECHNICAL FIELD

This invention relates to a method for preparing fatty acid alkyl ester using fatty acid, and more particularly to a method for preparing fatty acid alkyl ester for bio-diesels by reacting fatty acid, specifically fatty acid distillate with alcohol in the presence of metal catalyst instead of conventional acid or solid acid catalyst. The method does not require the glycerine purification process, and has the superior conversion ratio of fatty acid.

BACKGROUND ART

Diesel, among the various fuels derived from crude mineral oils, have advantages such as good fuel efficiency, low cost and low carbon dioxide generation. On the other hand, there is a problem that the combustion of diesel produces a large quantity of air pollution, especially particulates matters. In order to solve the problem, various researches have been conducted on alternative fuel which has similar physical property to diesel, and is economically preferable, and also can prevent the air pollution. The bio-diesel has similar physical property to diesel oil, remarkably reduces air pollution, and is naturally recycling energy source. Generally, the bio-diesel is produced by transesterification reaction of vegetable oil such as rapeseed oil, soybean oil, sunflower oil, palm oil, etc, animal fats, waste cooking oil, and so on with alcohol in the presence of acid catalyst or alkali catalyst. In the production of the bio-diesel, about 10 weight % of glycerin with respect to the total amount of bio-diesel is produced as a by-product. Recently, since the plant construction for bio-diesel is rapidly and world-widely progressed, an oversupply of glycerin is expected.

On the other hand, oils and fats generally contain free fatty acids, which exist in the mixed form with triglyceride of fatty acid. The free fatty acids are separated as the by-product in the refining process of oils and fats. Several methods for preparing fatty acid alkyl ester from the separated free fatty acids have been known. The methods for esterification of the free fatty acids are disclosed in European patent publication No. 127104A, European patent publication No. 184740A and U.S. Pat. No. 4,164,506, and so on. In the methods, the esterification reaction is carried out by heating the mixture of fatty acid and fatty acid triglyceride with methanol at about 65° C. in the presence of sulfuric acid or sulfonic acid catalyst. European patent publication No. 708813A discloses the method for increasing the yield of the fatty acid alkyl ester from oils and fats. In the method, the free fatty acid is separated from glycerin phase which is the product of transesterification reaction, and then the separated free fatty acid is esterified. In this method, the free fatty acid is obtained by the neutralization of glycerin phase, and the obtained free fatty acid is reacted for 2 hours at about 85° C. in the presence of strong sulfuric acid catalyst, which reduces the amount of fatty acid from 50% to 12%. In addition, a method for improving esterification reaction efficiency of fatty acid is disclosed (Korean patent unexamined-publication No. 2004-0101446, International Publication No. WO 2003/087278), which utilizes a mechanical apparatus or supersonic waves for causing dynamic turbulence in a reactor. In this method, the esterification is carried out by reacting the fatty acid and/or fatty acid contained in oils and fats with alcohol at a high pressure and a high temperature using sulfuric acid or ion exchange resin as catalyst. Further, Korean patent unexamined-publication No. 2004-87625 discloses a method for removing free fatty acid from waste cooking oil, using solid acid catalyst. The above mentioned methods commonly use an acid catalyst, such as sulfuric acid etc. If such an acid catalyst is not completely removed after the reaction, the quality of bio-diesel is deteriorated. Therefore, complicate processes for neutralizing, filtering, washing and cleaning the acid catalyst must be needed, and there is the defect of high cost for production facilities because of corrosion resistance quality of reactors. Also, the life cycle of the solid acid catalyst is generally not so long that cost for recycling the same is too much expensive. Furthermore, in the above mentioned conventional methods, since the esterification of fatty acid is carried out at low temperature, water produced during the reaction is not efficiently removed to outside of the reaction system. Thus, the conversion ratio of fatty acid into fatty acid alkyl ester is low, and the physical properties of the obtained fatty acid alkyl ester are not suitable for bio-diesel. Besides, the Korean Patent Application No. 10-2006-38872 of the present applicant discloses a method and an apparatus for solving the above mentioned defects, but the method and the apparatus does not use catalyst, and the reaction rate is not satisfactory.

DISCLOSURE

Technical Problem

Therefore, it is an object of the present invention to provide a method for preparing fatty acid alkyl ester suitable for bio-diesel fuel.

It is another object of the present invention to provide a method for preparing fatty acid alkyl ester by esterifying fatty acid with alcohol at high temperature range with using metal catalyst which does not affect the quality of the product and is easily removed as residues by a purification. The method is different from the conventional method for preparing fatty acid alkyl ester and glycerin by carrying out the transesterification reaction of vegetable oils or animal fats with alcohol in the presence of acid or solid acid catalyst.

It is still another object of the present invention to provide a method for conveniently and economically preparing fatty acid alkyl ester without producing glycerin, by using fatty acid distillate as a raw material, which is generated as a by-product during the refining process of vegetable oils.

Technical Solution

In order to achieve these objects, the present invention provides a method for preparing fatty acid alkyl ester for bio-diesel fuels, which comprises the step of carrying out an esterification reaction of fatty acid raw material with alcohol in the presence of metal catalyst. Preferably, the esterification reaction is carried out at the temperature of 200 to 350° C. and the pressure of atmospheric pressure to 10 bar, and the metal catalyst is a compound containing metal selected from the group consisting of cobalt, iron, manganese, zinc, titanium and mixture thereof.

Advantageous Effects

In the method for preparing fatty acid alkyl ester of the present invention, fatty acid and alcohol reacts under a predetermined high temperature and pressure, in the presence of metal catalyst. Therefore, the neutralizing, filtering, washing and cleaning processes for removing the catalyst are not required. In the present invention, fatty acid alkyl ester of high purity and high conversion ratio can be obtained by two-step distillation processes. Thus the total process for producing fatty acid alkyl ester is simplified and cost for process facilities and the operation thereof is reduced. Moreover, the present invention is economically favorable since worthless fatty acid distillate and/or cheap fatty acid are used as the raw material. In the present invention, the by-product, such as glycerin is not produced, and excess alcohol can be recovered and reused.

MODE FOR INVENTION

A more complete appreciation of the invention, and many of the attendant advantages thereof, will be better appreciated with reference to the following detailed description and the accompanying drawings.

Figure 1:
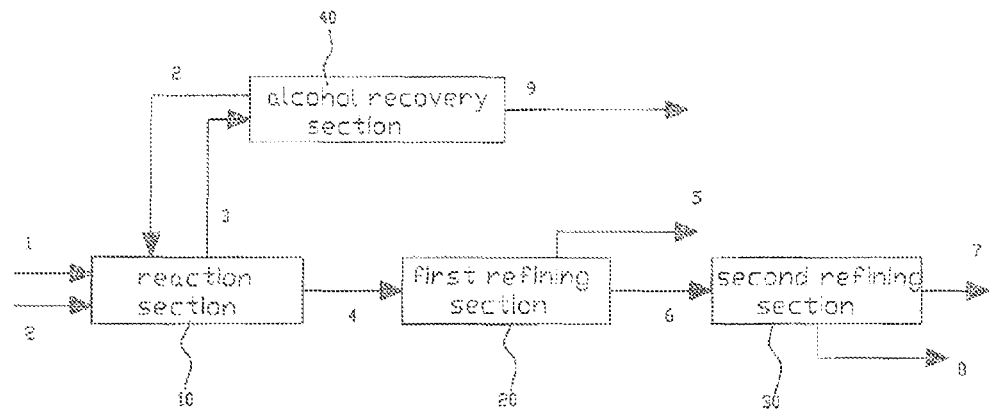
FIG. 1 is a drawing for showing the entire configuration of the apparatus for preparing fatty acid alkyl ester according to an embodiment of the present invention.

FIG. 1 shows the entire configuration of the apparatus which can be used for the method for preparing fatty acid alkyl ester according to an embodiment of the present invention. As shown in FIG. 1, fatty acid raw material 1 (hereinafter, if necessary, simply "fatty acid") and alcohol 2 are introduced into a reaction section 10 and then esterification reaction is carried out at a predetermined temperature and pressure. The crude fatty acid alkyl ester 4 produced at the esterification reaction is transferred to the first refining section 20, and the impurities 5 having low boiling point can be removed through the top of the distillation column of the first refining section 20 by distillation. The first refined fatty acid alkyl ester 6 is transferred to the second refining section 30, and distilled to leave residues (residual impurities 8 such as metal catalyst used in the reaction) in the second refining section 30. The distilled and purified fatty acid alkyl ester 7 is discharged through the top of the distillation column of the second refining section 30. On the other hand, the reaction section 10 is connected to an alcohol recovery section 40 so that a mixture (alcohol/water 3) of water produced at the reaction section 10 and excess alcohol which is unreacted at the reaction section 10, is introduced into the alcohol recovery section 40. In the alcohol recovery section 40, the alcohol 2 is distillated and recycled to the reaction section 10 and water 9 is transferred to a waste water disposal plant.

In the present invention, as the fatty acid raw material 1 for preparing fatty acid alkyl ester 7, pure fatty acid (RCOOH) in which carbon atom number of aliphatic part (R) is 14 to 24, can be used. However, it is preferable to use fatty acid distillate as the raw material. The fatty acid distillate is produced as a by-product during the process of refining crude vegetable oil collected from vegetables such as rapeseed, soybean, sunflower, palm, or so on. The refining process can be carried out by a high pressure steam to obtain refined vegetable oil, such as rapeseed oil, soybean oil, sunflower oil or palm oil, or so on. If necessary, a mixture of the pure fatty acid and the fatty acid distillate can be used. The fatty acid distillate generally contains 65 to 95 weight %, preferably 80 to 85 weight % of the fatty acid in which carbon atom number of aliphatic part (R) is 14 to 24. The remaining components of the fatty acid distillate include β-carotin, fatty acid in which carbon atom number of aliphatic part (R) is less than 14 or more than 24, and so on. In the method for preparing fatty acid alkyl ester according to the present invention, it is economically advantageous to use the fatty acid distillate as the raw material. As the alcohol for the present invention, monovalent alcohols having 1 to 10 carbon atoms, preferably monovalent alcohols having 1 to 4 of carbon atom such as methanol, ethanol, propanol, or so on, and more preferably methanol, can be used.

The method for preparing fatty acid alkyl ester of the present invention is carried out in the presence of metal catalyst. Example of the metal catalyst includes a compound containing metal selected from the group consisting of cobalt, iron, manganese, zinc, titanium, antimony, germanium, zirconium, lead, and mixtures thereof. The preferable metal catalyst includes acetate, oxide, alkoxide, hydroxide, carbonate or so on of the above mentioned metal. Examples of the metal catalyst include cobalt acetate, manganese acetate, zinc acetate, iron acetate, germanium dioxide, tetrabutyl titanate and so on. Preferably, the metal catalyst is added to the esterification reaction in the form of alcohol solution. Preferably, the metal catalyst is added to the esterification reaction so that the amount of metal in the catalyst is 30 to 200 ppm, preferably 50 to 100 ppm (by weight) with respect to the fatty acid raw material. If the amount of the metal catalyst is less than the above mentioned range, it is economically undesirable because of the slow reaction rate. If the amount of metal catalyst used is more than the above mentioned range, the reaction rate does not further increase, but it is economically unfavorable. Meanwhile, if the fatty acid raw material contains impurities such as phosphorus (P) which inhibit the activity of the metal catalyst, it is desirable to increase the amount of the metal catalyst according to the amount of impurities. When adding the metal catalyst to a reactor in the alcohol solution, the amount of alcohol can be controlled so as to completely dissolve the metal catalyst.

Figure 2:
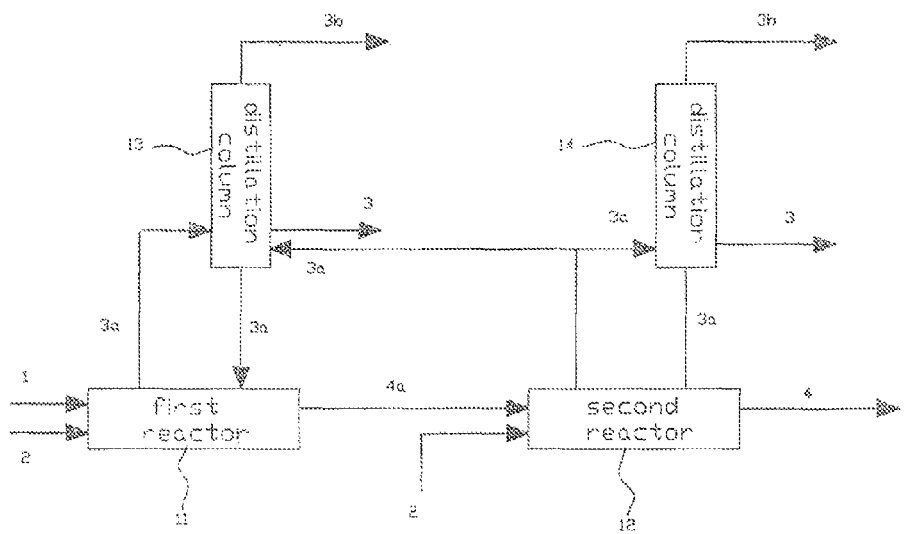
FIG. 2 is a drawing for showing an embodiment of the reaction section depicted in FIG. 1.

In the present invention, the esterification reaction can be carried out in one-step or two-steps. In the one-step esterification reaction, the reaction section 10 is constituted by one reactor and one distillation column. In the two-step esterification reaction, the reaction section 10 may be constituted by two reactors and one distillation column where the one distillation column is commonly used, or one reactor and one distillation column can be used for each step as shown in FIG. 2. Moreover, the reactor and the distillation column may not be separated, but can be integrated, wherein the lower part of the integrated apparatus works as the reactor, and the upper part of the integrated apparatus works as the distillation column. In this case, a seal tray can be installed between the upper part for the distillation column and the lower part for the reactor to prevent water from falling from the upper part to the lower part. The esterification reaction according to the present invention can be carried out by a batch process or a continuous process, and carried out by one-step or two-steps as previously described. In the continuous process, if the retention (stay) time is sufficient, the one-step reaction can provide a sufficiently high conversion ratio, however it is preferable to carry out the two-step reaction. In case of the batch process, if the conversion ratio of the first reaction is insufficient, the conversion ratio can be improved by carrying out the second reaction with modified reaction conditions.

FIG. 2 shows an embodiment of the reaction section 10 in FIG. 1, which is constituted by two reactors 11, 12 and two distillation columns 13, 14. Referring to FIG. 2, a product 4a which is obtained by the reaction in the first reactor 11 is introduced into the second reactor 12 together with alcohol 2 for the second reaction in the second reactor 12. The crude fatty acid alkyl ester 4 which is the product of the second reaction in the second reactor 12 is transferred the refining sections 20, 30 in FIG. 1. The mixtures 3a containing water produced at each reactor 11, 12 and the excess alcohol which is unreacted are exhausted into the distillation columns 13, 14, respectively. The mixture 3a is separated in the distillation columns 13, 14 so that pure alcohol or the azeotrope of alcohol/water 3b is exhausted via the upper part of the distillation columns 13, 14 and the mixture 3 containing alcohol and water, in which the concentration of water is high, is exhausted through the lower part of the distillation columns 13, 14. Here, the pure alcohol or the azeotrope of alcohol/water 3b obtained at the upper part of the distillation columns 13, 14 can be reused as an alcohol which is introduced into the reaction section 10. The alcohol/water mixture 3, in which the concentration of water is high, is transferred to the alcohol recovery section 40 of FIG. 1.

Hereinafter, the preparation conditions of fatty acid alkyl ester according to the present invention will be described in detail. The metal catalyst is introduced in the esterification reaction of the present invention, and the esterification reaction is carried out at high temperature. Thus, high reaction rate and high conversion ratio of fatty acid into fatty acid alkyl ester can be obtained in the present invention. The temperature for the esterification reaction of the present invention is 200 to 350° C., preferably 250 to 320° C. The pressure for the esterification reaction of the present invention is atmospheric pressure to 10 bar, preferably atmospheric pressure to 5 bar. The esterification reaction according to the present invention can be carried out by the batch process or the continuous process. In case of the batch process, the esterification reaction may be performed while maintaining the constant pressure of atmospheric pressure to 10 bar. Alternatively, the initial esterification reaction is carried out at a relatively high pressure of 3 bar to 10 bar to increase the reaction rate, and then the latter esterification reaction is carried out at a relatively low pressure of atmospheric pressure to 3 bar to remove the produced water from the reactant, thereby enhancing the conversion ratio of the reaction. Preferably, the metal catalyst is dissolved in alcohol, and the solution is added to a reactor with fatty acid simultaneously. In case of the continuous process, the pressure in all reaction procedure may be the constant pressure of atmospheric pressure to 10 bar, or the first reactor of the two-step reaction is maintained at a pressure of 3 bar to 10 bar and the second reactor of the two-step reaction is maintained at a pressure of atmospheric pressure to 3 bar. If the reaction temperature and the reaction pressure are not within the above mentioned ranges, the reaction rate and the conversion ratio of fatty acid are reduced or adverse side reactions may occur. In case of the continuous process, the metal catalyst dissolved in alcohol can be continuously added to the reactor with fatty acid.

Since the conventional esterification reaction of fatty acid using acid catalyst or solid acid catalyst is carried out at low temperature of less than 100° C. and water produced during the esterification reaction cannot be removed from the reaction system, the esterification reaction cannot be progressed beyond the reaction equilibrium. However, the esterification reaction of the present invention is performed at high temperature of 200 to 350° C. Thus, water produced during the esterification reaction can be continuously removed from the reaction system together with excess alcohol. Accordingly, the esterification reaction according to the present invention is progressed beyond the reaction equilibrium so that the conversion ratio of fatty acid is excellent near to the complete reaction. Specifically, in order to use the fatty acid alkyl ester as the bio-diesel, the total acid number (mg KOH/g) of the fatty acid alkyl ester should be less than a predetermined value. However, if the unreacted fatty acid component (carbon atom number of aliphatic part is 14 to 24) remains, the total acid number (mg KOH/g) of the produced fatty acid alkyl ester becomes high, and the fatty acid alkyl ester cannot satisfy the quality criteria for the bio-diesel. Since the unreacted fatty acid component have similar boiling point with fatty acid methyl ester, it is very difficult for the unreacted fatty acid component to be separated by the distillation. Thus, the unreacted fatty acid component should be prevented by the complete esterification reaction. The method for preparing fatty acid alkyl ester according to the present invention has more than 99.7% of the conversion ratio of fatty acid into fatty acid alkyl ester, which satisfy the total acid number quality criteria for the bio-diesel. On the other hands, with the conventional method for preparing fatty acid alkyl ester using acid catalyst or solid acid catalyst, it is difficult to increase the conversion ratio of fatty acid to be more than 99.7%. Also, in the method for producing fatty acid alkyl aster of the present invention, the acid catalyst used is not used, and the expensive production facilities durable to acid catalyst are unnecessary.

In the continuous process, alcohol is introduced by an amount of about 0.5 to 5 times by weight, preferably 1 to 3 times by weight, with respect to the introduced amount of fatty acid. Preferably, the metal catalyst is dissolved in the alcohol, and added to the reactor in the amount of 30 to 200 ppm (based on the metal component) by weight ratio with respect to fatty acid. The retention time of the total reaction process is 1 to 10 hours, preferably 3 to 5 hours. If the introduced amount of alcohol deviates from the above mentioned range, the reaction rate and the reaction yield can be reduced and it is economically undesirable. In the batch process, fatty acid, alcohol and the metal catalyst dissolved in the alcohol are initially introduced into a reactor, wherein the amount of alcohol is 0.1 to 3 times by weight with respect to amount of fatty acid and the amount of the metal catalyst dissolved in the alcohol is 30 to 200 ppm (based on the metal component) by weight ratio with respect to fatty acid. When the temperature and pressure of the reactor reaches predetermined temperature and pressure, alcohol for inducing main reaction is introduced into the reactor. In this case, the total amount of alcohol to be introduced during the total reaction time is 0.5 to 5 times by weight, preferably 1 to 3 times by weight with respect to the amount of fatty acid. The reaction time is 1 to 10 hours, preferably 3 to 5 hours. Also, at the latter (second half) period of the reaction of the continuous process or the batch process, if the introduced amount of alcohol increases by 1 to 3 times, preferably 1.5 to 3 times with respect to the initial introduced amount of alcohol, the reaction conversion ratio can be further improved.

The exemplary esterification reactor for the present invention includes a continuous stirred tank reactor (CSTR type) on which a stirrer is installed, a plug flow reactor (PFR) in which a baffle is mounted for providing a sufficient retention time, or so on. In a preferable reactor, at least one comparting wall is installed in the reactor to divide the interior of the reactor into several compartments. In the preferable reactor, reactants consecutively overflow the comparting wall to be consecutively transferred to the adjacent compartment, which provides sufficient retention time.

Figure 3:
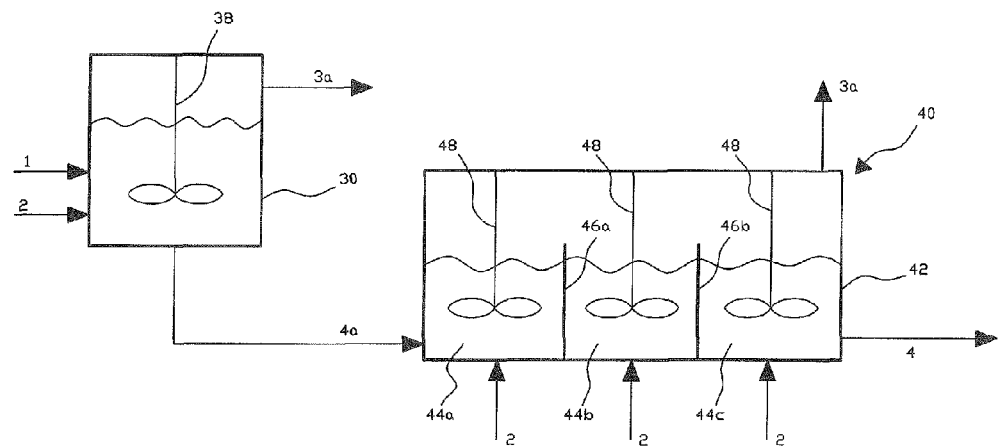
FIG. 3 and FIG. 4 are drawings for showing embodiments of the reactor which can be used for a method for preparing fatty acid alkyl ester according to the present invention.
Figure 4:
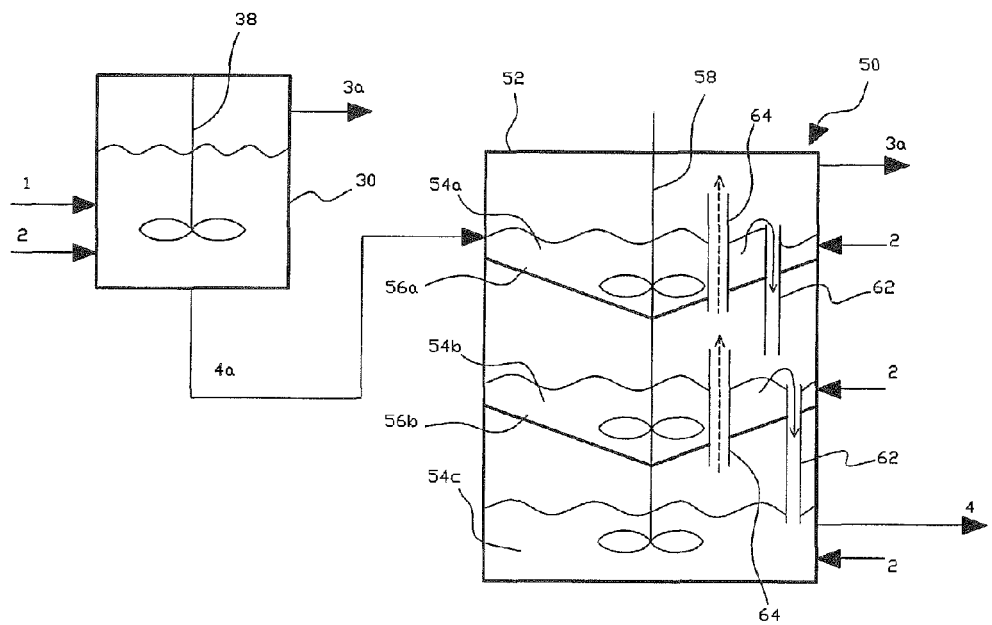

FIG. 3 and FIG. 4 show preferable embodiments of the reactor which can be used as the apparatus for preparing fatty acid alkyl ester according to the present invention. As shown in FIG. 3, the esterification reactor for the present invention includes the first reactor 30 for converting 80 to 90% of the total fatty acid to fatty acid alkyl ester and the second reactor 40 for converting the remaining fatty acid which is not converted in the first reactor 30 to fatty acid alkyl ester. The raw materials, fatty acid 1 and alcohol 2 are introduced into the first reactor 30 for the first reaction. The product 4a of the first reaction is extracted through the lower part of the first reactor 30 and the mixture 3a containing water produced at the first reaction and the excess alcohol which is unreacted at the first reaction, is extracted in gas phase through the upper part of the first reactor 30. The second reactor 40 includes a reactor body 42 and at least one computing wall 46a, 46b. The comparting walls 46a, 46b divide the interior of the reactor 40 into two or more compartments 44a, 44b, 44c, wherein the upper parts of the computing walls 46a, 46b are open so that the reactants overflow over the comparting walls 46a, 46b. The divided compartments 44a, 44b, 44c of the second reactor 40 can be formed on the same plane and the adjacent compartments 44a, 44b, 44c can be liquid flowably connected to each other via the upper part of the comparting walls 46a, 46b. Accordingly, the product 4a of the first reaction and alcohol 2 are introduced into the first compartment 44a, and sufficiently react in the first compartment 44a. As the introduced amount of the product 4a increases, the product 4a flows into the second compartment 46b over the first comparting wall 44a. In the second compartment 44b, the product 4a again reacts with alcohol 2 and then overflows into the third compartment 44c over the second comparting wall 46b. In the third compartment 44c, the product 4a reacts again with alcohol 2 and is converted into crude fatty acid alkyl ester 4. Then the crude fatty acid alkyl ester 4 is extracted from the second reactor 40. At this time, the mixture 3a containing water produced during the reaction and alcohol is exhausted via the upper part of the second reactor 40. In addition, stirrers 38, 48 for stirring the reactants may be installed in the first reactor 30 and in the compartments 44a, 44b, 44c of the second reactor 40.

The esterification reactor shown in FIG. 4 includes the first reactor 30 for converting 80 to 90% of the total fatty acid to fatty acid alkyl ester and the second reactor 50 for converting remaining fatty acid which is not converted in the first reactor 30 to fatty acid alkyl ester. The first reactor 30 has the same structure described in FIG. 3. The second reactor 50 includes a reactor body 52 and at least one comparting wall 56a, 56b. The comparting walls 56a, 56b divide the interior of the second reactor 50 into two or more compartments 54a, 54b, 54c. The compartments 54a, 54b, 54c in the second reactor 50 are arranged in the form of vertical stack, and the comparting walls 56a, 56b form the bottom plates of the compartments 54a, 54b. Namely, the first compartment 54a and the second compartment 54b, which is located under the first compartment 54a, are divided by the first comparting wall 56a. A liquid guide path 62 and a gas guide path 64 are installed on the first comparting wall 56a. The liquid guide path 62 and the gas guide path 64 penetrate the first comparting wall 56a. One end of the liquid guide path 62 is located at the height corresponding to the surface of reactants located in the first compartment 56a, and the other end of the liquid guide path 62 is located at the height which is higher than the surface of reactants located in the second compartment 54b. One end of the gas guide path 64 is located at the height which is higher than the surface of reactant located in the first compartment 54a, and the other end of the gas guide path 64 is located at the height which is higher than the surface of reactant located in the second compartment 54b. The liquid guide path 62 and the gas guide path 64 are installed on each comparting walls 56a, 56b in the above described manner. Thus, the vertically adjacent compartments 54a, 54b, 54c are communicated with each other via the liquid guide path 62 and the gas guide path 64 installed on the comparting walls 56a, 56b. As a result, the product 4a of the first reaction and alcohol 2 are introduced into the first compartment 54a, and sufficiently react in the first compartment 54a. As the introduced amount of the product 4a of the first reaction increases, the product of first compartment 54a overflows via the liquid guide path 62 into the second compartment 54b to react with alcohol 2 introduced into the second compartment 54b and again overflows into the third compartment 54c via the liquid guide path 62 installed on the second comparting wall 56b. In the third compartment 54c, the product of second compartment 54b reacts with alcohol 2 and is converted into crude fatty acid alkyl ester 4. The crude fatty acid alkyl ester 4 is extracted from the second reactor 50. At this time, the mixture 3a containing water produced during the reaction and excess alcohol sequentially moves to the upper compartments 54b, 54a via the gas guide path 64, and finally exhausted from the second reactor 50 through the upper part of the first compartment 54a.

As described above, in the present invention, 80 to 90% of the total fatty acid is converted to fatty acid alkyl ester in the first reactor 30, and remaining unconverted fatty acid is converted to fatty acid alkyl ester in the second reactor 40, 50 while sequentially passing the adjacent compartments of the second reactor 40, 50. Thus, the retention time of the fatty acid can be prolonged, and the conversion ratio of fatty acid into fatty acid alkyl ester (conversion of the reaction) can be improved.

The most part of the crude fatty acid alkyl ester 4 obtained by esterification reaction of the present invention is fatty acid alkyl ester. However, in order to use the fatty acid alkyl ester of the present invention as industrial fuels or bio-diesel fuels, low molecular weight fatty acid alkyl esters, high molecular weight fatty acid alkyl esters, residues, and so on should be removed from the crude fatty acid alkyl ester 4. Especially in case of fatty acid methyl ester, fatty acid alkyl ester having carbon atom number of aliphatic part being less than 14 or more than 24 and other low molecular weight impurities should be removed, so as to satisfy the quality criteria of the bio-diesel. Therefore, in the present invention, the crude fatty acid alkyl ester 4 is refined by the two-step distillation process. Referring to FIG. 1, in the first refining section 20 of the present invention, 1 to 10 weight %, preferably 2 to 5 weight % of an introduced amount (feed) is removed through the upper part of a distillation column by maintaining the temperature of the lower part of the distillation column to be 150 to 250° C., preferably 180 to 220° C. at the vacuum condition of 0.1 to 150 torr, preferably 0.1 to 40 torr. When the amount removed through the upper part of the distillation column is less than 1 weight % of the feed, impurities having low boiling point cannot be sufficiently removed. When the amount removed through the upper part of the distillation column is more than 10 weight % of the feed, the yield may be reduced. In this case, most of the impurities of low boiling point which are removed through the upper part of the distillation column are low molecular weight fatty acid alkyl ester. Thus, the removed impurities can be directly used as fuels for boilers, etc, without additional process. In the second refining section 30 of the present invention, the impurities of 1 to 25 weight % of an introduced feed are left for removal in the lower part of the distillation column, and the refined fatty acid alkyl ester of high purity is extracted through the upper part of the distillation column by maintaining the temperature of the lower part of the distillation column to be 200 to 300° C., preferably 220 to 280° C. at the vacuum condition of 0.1 to 150 torr, preferably 0.1 to 40 torr. The amount of the removed impurities (residue) can be varied according to the composition of the fatty acid raw material. However, when the amount remaining on the lower part of the distillation column is less than 1 weight % of the feed, the purity of fatty acid alkyl ester can be deteriorated. When the amount remaining on the lower part of the distillation column is more than 25 weight % of the feed, the distillation yield may be reduced. Here, most of the remaining impurities are fatty acid alkyl ester having carbon atom number of aliphatic part being more than 24. Thus, the remaining impurities can be used as fuels for boilers, etc. Besides, the metal catalyst used in reaction is extracted with the residue and does not deteriorate the quality of fatty acid alkyl ester. Then, the metal catalyst extracted with residue may be discarded or may be reused by recycling after combustion. The fatty acid alkyl ester refined by the above mentioned method, specifically fatty acid methyl ester satisfies all quality criteria on the bio-diesels in Korea and foreign major countries including U.S.A. and Europe. Therefore, the fatty acid alkyl ester of the present invention can be directly used as bio-diesel.

On the other hand, water produced during the esterification reaction of the present invention is extracted from the reaction section 10 together with excess alcohol which is unreacted in the esterification reaction, and the mixture is separated at the alcohol recovery section 40. After separation, water is transferred to the waste water disposal plant, and the alcohol is recycled to the reaction section 10 for reuse. The alcohol recovery section 40 includes a distillation column and affiliated facilities therefor. The temperature of the lower part of the distillation column of the alcohol recovery section 40 is controlled according to the boiling point of alcohol so as to distil alcohol. The distilled and reused alcohol can contain 0 to 10 weight %, specifically 0.001 to 10 weight % of water. If the amount of water contained in alcohol is more than 10 weight %, the esterification rate in the reaction section 10 may be reduced. Also, in case of using methanol, by only using single distillation column, methanol can be refined with sufficiently high purity and can be recycled to the reaction section 10. In case of using alcohol having at least 2 carbon atoms, for example, ethanol, the alcohol/water azeotrope is extracted from the distillation column of the alcohol recovery section 40, and is subject to dehydration process to remove water. Then the water removed alcohol is recycled to the reaction section 10.

Hereinafter, the preferable examples are provided for better understanding of the present invention. However, the present invention is not limited to the following examples.

EXAMPLE 1

Preparation of Fatty Acid Methyl Ester (Continuous Process)

The esterification reaction was carried out by two-step reaction using the reactors shown in FIG. 3. Firstly, the first reactor was controlled to temperature of 300° C. and pressure of 3 bar. 1 kg of fatty acid distillate, which is obtained by distilling crude palm oil, and 1 kg of methanol containing 0.2 g of cobalt acetate, were continuously introduced into the reactor and retention time of the reaction in the first reactor was 1 hour. And reactant of the first reactor was continuously introduced into second reactor. Then, the temperature of the second reactor was maintained to be same with that of the first reactor, and the pressure was reduced to atmospheric pressure, and retention time of the reaction in the second reactor was 1 hour. For the reaction in the second reactor, 2 kg of methanol (two times of the first feed amount) was divided by 3, and each divided part was continuously introduced into each compartment 44a, 44b, 44c. The conversion ratio for fatty acid methyl ester by the above mentioned method was 99.7% (total acid number: less than 0.4). The total termination time (the total residence time) of the reaction was reduced to 50% of the reaction time without catalyst.

EXAMPLE 2

Preparation of Fatty Acid Methyl Ester (Batch Process)

The esterification reaction was carried out by one-step reaction using a batch reactor. Firstly, 1 kg of fatty acid distillate and 0.5 kg of methanol containing 0.8 g of tetrabutyl titanate were introduced into the reactor. The reactor was controlled to temperature of 300° C. and pressure of 3 bar, and 1 kg of methanol was further added to the reactor, and the reaction was carried out for 1.5 hours. The conversion ratio for fatty acid methyl ester by the above mentioned method was 99.8%. The total time to complete the reaction is 1.5 hr which is lower by 50% with respect to the reaction time without catalyst.

Industrial Applicability

The method for preparing the fatty acid alkyl ester according to the present invention can be applicable to the manufacturing apparatus of an industrial scale as well as of a small scale. Especially, the fatty acid methyl ester prepared according to the present invention can be directly used as the bio-diesel without additional process.

The invention claimed is:

1. A method for preparing a fatty acid alkyl ester for bio-diesel fuels, comprising the step of carrying out an esterification reaction of a fatty acid raw material with an alcohol in the presence of a metal catalyst,
    wherein the esterification reaction is carried out at a temperature of 200 to 350° C. and a pressure of atmospheric pressure to 10 bar, and the metal catalyst is used so that the amount of metal in the catalyst is 30 to 200 ppm (by weight) with respect to the fatty acid, and
    wherein the metal catalyst is selected from the group consisting of cobalt acetate, manganese acetate, zinc acetate, iron acetate, germanium dioxide, tetrabutyl titanate, and mixtures thereof.

2. The method for preparing the fatty acid alkyl ester of claim 1, wherein the metal catalyst is added to the esterification reaction in the form of an alcohol solution.

* * * * *